(12) United States Patent
Tan et al.

(10) Patent No.: US 7,301,026 B2
(45) Date of Patent: Nov. 27, 2007

(54) PROCESS FOR MAKING FLUORINATED 4-AZASTEROID DERIVATIVES

(75) Inventors: Lushi Tan, Edison, NJ (US); Benjamin T. Dorner, Hoboken, NJ (US); Wenjie Li, Edison, NJ (US); Nobuyoshi Yasuda, Mountainside, NJ (US); Frederick W. Hartner, Somerville, NJ (US)

(73) Assignee: Merck & Co., Inc, Rahway, NJ (US)

( * ) Notice: Subject to any disclaimer, the term of this patent is extended or adjusted under 35 U.S.C. 154(b) by 0 days.

(21) Appl. No.: 11/410,179

(22) Filed: Apr. 24, 2006

(65) Prior Publication Data

US 2006/0252937 A1    Nov. 9, 2006

Related U.S. Application Data

(60) Provisional application No. 60/677,922, filed on May 5, 2005, provisional application No. 60/707,198, filed on Aug. 10, 2005.

(51) Int. Cl.
   *C07D 221/18*    (2006.01)
(52) U.S. Cl. ...................................................... 546/77
(58) Field of Classification Search ................. 546/61, 546/77, 118
   See application file for complete search history.

(56) References Cited

U.S. PATENT DOCUMENTS 7,186,838 B2 *   3/2007   Meissner et al. ............. 546/77

OTHER PUBLICATIONS

King, A.O. et al., J. Org. Chem. 1993, vol. 58, pp. 3384-3386.
Lal, G.S. et al., J. Org. Chem. 1999, vol. 64, pp. 7048-7054.
Pogany, S.A. et al., Synthesis, 1987, vol. 8, pp. 718-719.
Wilkinson, J.A., Chem. Rev., 1992, vol. 92, pp. 505-519.

* cited by examiner

*Primary Examiner*—D. Margaret Seaman
*Assistant Examiner*—Nizal S. Chandrakumar
(74) *Attorney, Agent, or Firm*—Curtis C. Panzer; Patricia A. Shatynski

(57) ABSTRACT

The present invention relates to synthetic processes useful in the preparation of fluorinated 4-azasteroid derivatives that modulate androgen receptors and have application in the treatment of conditions caused by androgen deficiency or androgen receptor hyperactivity, such as osteoporosis, periodontal disease, bone fracture, frailty, erectile dysfunction, loss of libido, androgen-dependent cancers and sarcopenia. The present invention also encompasses intermediates useful in the disclosed synthetic processes and the methods of their preparation.

3 Claims, No Drawings

PROCESS FOR MAKING FLUORINATED 4-AZASTEROID DERIVATIVES

CROSS REFERENCE TO RELATED APPLICATIONS

This application claims the benefit of U.S. No. 60/677,922, filed May 5, 2005 and also claims the benefit of 60/707,198 filed Aug. 10, 2005.

FIELD OF THE INVENTION

The present invention relates to synthetic processes useful in the preparation of fluorinated 4-azasteroid derivatives that modulate androgen receptors and have application in the treatment of conditions caused by androgen deficiency or androgen receptor hyperactivity, such as osteoporosis, periodontal disease, bone fracture, frailty, erectile dysfunction, loss of libido, androgen-dependent cancers and sarcopenia. The present invention also encompasses intermediates useful in the disclosed synthetic processes and the methods of their preparation.

BACKGROUND OF THE INVENTION

The androgen receptor (AR) belongs to the superfamily of steroid/thyroid hormone nuclear receptors, whose other members include the estrogen receptor (ER), the progesterone receptor (PR), the glucocorticoid receptor (GR), and the mineralocorticoid receptor (MR). The AR is expressed in numerous tissues of the body and is the receptor through which the physiological, as well as the pathophysiological, effects of endogenous androgen ligands, such as testosterone (T) and dihydrotestosterone (DHT), are expressed. A compound that binds to the AR and mimics the effects of an endogenous AR ligand is referred to as an AR agonist, whereas a compound that inhibits the effects of an endogenous AR ligand is termed an AR antagonist.

The therapeutic usefulness of compounds that modulate AR, either as antagonists or as agonists, has been established by clinical studies involving a variety of disorders in both men and women. In men, drugs targeting the AR have found application in conditions related to reproductive disorders and primary or secondary male hypogonadism. A number of AR agonists, both naturally occurring and synthetic, have been clinically investigated for the treatment of musculoskeletal disorders, such as bone disease, hematopoietic disorders, neuromuscular disease, rheumatological disease, and wasting disease, as well as part of hormone replacement therapy (HRT) in cases of female androgen deficiency. In addition, AR antagonists, such as flutamide and bicalutamide, have been used to treat prostate cancer.

The beneficial effects of androgens on bone in postmenopausal osteoporosis have been documented in studies using combined testosterone and estrogen administration [Hofbauer, et al., "Androgen effects on bone metabolism: recent progress and controversies," *Eur. J. Endocrinol.* 140: 271-286 (1999)]. It is also well established that androgens play an important role in bone metabolism in men, which parallels the role of estrogens in women [Anderson, et al., "Androgen supplementation in eugonadal men with osteoporosis—effects of six months of treatment on bone mineral density and cardiovascular risk factors," *Bone*, 18: 171-177 (1996)]. The delitirous effects of androgen deprivation are exemplified in a study of men with stage D prostate cancer. In this study, osteopenia (50% vs. 38%) and osteoporosis (38% vs. 25%) were more common in men who had undergone androgen deprivation therapy (ADT) for greater than one year than the patients who had not undergone ADT [Wei, et al., "Androgen deprivation therapy for prostate cancer results in significant loss of bone density," *Urology*, 54: 607-611 (1999)].

AR antagonists have also been found useful in the treatment of polycystic ovarian syndrome in postmenopausal women [see C. A. Eagleson, et al., "Polycystic ovarian syndrome: evidence that flutamide restores sensitivity of the gonadotropin-releasing hormone pulse generator to inhibition by estradiol and progesterone," *J. Clin. Endocrinol. Metab.*, 85: 4047-4052 (2000) and E. Diamanti-Kandarakis, "The Effect of a Pure Antiandrogen Receptor Blocker, Flutamide, on the Lipid Profile in the Polycystic Ovary Syndrome," *Int. J. Endocrinol. Metab.*, 83: 2699-2705 (1998).] Additional uses and rationales for the development of androgen receptor modulators may be found in L. Zhi and E. Martinborough in *Ann. Rep. Med. Chem.* 36: 169-180 (2001). The relationship between molecular structure and the antagonistic or agonistic activity of non-steroidal AR compounds has also been the subject of numerous publications, such as J. P. Edwards, "New Nonsteroidal Androgen Receptor Modulators Based on 4-(Trifluoromethyl)-2(1H)-Pyrrolidino[3,2-g]quinolinone," *Bioorg. Med. Chem. Lett.*, 8: 745-750 (1998) and in L. Zhi et al., "Switching Androgen Receptor Antagonists to Agonists by Modifying C-ring Substituents on Piperidino[3,4-g]quinolinone," *Bioore. Med. Chem. Lett.*, 9: 1009-1012 (1999).

The established clinical usefulness makes the AR compounds highly desireable targets. A need therefore exists for chemical processes that can be used to make naturally occurring and synthetic AR-compounds. The present invention addresses this need.

These compounds are effective as androgen receptor agonists and are particularly effective as selective androgen receptor agonists (SARMs). They are therefore useful for the treatment of conditions caused by androgen deficiency or which can be ameliorated by androgen administration.

International application WO03/077919, published on Sep. 25, 2003, which is incorporated by reference in its entirety, describes fluorinated 4-azasteroidal derivatives that are useful in the enhancement of weakened muscle tone and the treatment of conditions caused by androgen deficiency or which can be ameliorated by androgen administration, including osteoporosis, osteopenia, glucocorticoid-induced osteoporosis, periodontal disease, bone fracture, bone damage following bone reconstructive surgery, sarcopenia, frailty, aging skin, male hypogonadism, postmenopausal symptoms in women, atherosclerosis, hypercholesterolemia, hyperlipidemia, obesity, aplastic anemia and other hematopoietic disorders, inflammatory arthritis and joint repair, HIV-wasting, prostate cancer, benign prostatic hyperplasia (BPH), abdominal adiposity, metabolic syndrome, type II diabetes, cancer cachexia, Alzheimer's disease, muscular dystrophies, cognitive decline, sexual dysfunction, sleep apnea, depression, premature ovarian failure, and autoimmune disease, alone or in combination with other active agents.

SUMMARY OF THE INVENTION

The present invention relates to chemical processes useful in the synthesis of compounds that are androgen receptor modulators. The present invention also encompasses chemical processes that afford intermediates useful in the production of androgen receptor modulators. The chemical processes of the present invention afford advantages over previously known procedures and include a convergerent, more efficient route to androgen receptor modulators.

DETAILED DESCRIPTION OF THE INVENTION

An embodiment of the present invention relates to a process for preparing an imidazopyridine methanamine of Formula I,

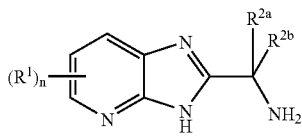

I or a hydrochloride salt thereof, which comprises:
(1) coupling an N-protected glycine derivative of Formula II and a 2,3-diaminopyridine of Formula III with an acid chloride activating agent to form an adduct of Formula IV; and

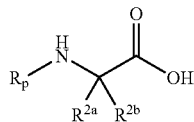

II

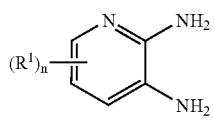

III

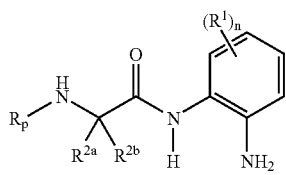

IV (2) cyclizing adduct IV by treating with an acid and deprotecting to afford the imidazopyridine methanamine of Formula I, wherein n is 0, 1, 2, or 3;
$R^1$ is independently $C_1$-$C_6$ alkyl, halo, $C_1$-$C_3$ perfluoroalkyl, $C_1$-$C_3$ alkyl(CO), or $C_1$-$C_6$ alkyloxy;
$R^{2a}$ and $R^{2b}$ are independently H, $C_1$-$C_6$ alkyl, $C_1$-$C_3$ perfluoroalkyl, or halo; and
$R_p$ is a nitrogen protecting group.

Another embodiment of the invention is illustrated by a process for preparing a 2-fluorolactam of Formula V,

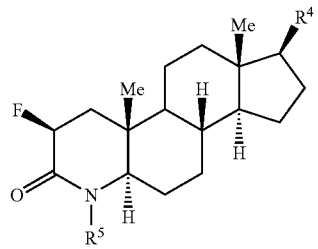

V which comprises treating a 2-iodolactam of Formula VI

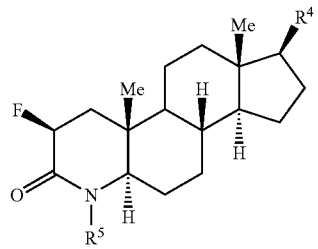

VI with silver(I) fluoride, wherein R4 is

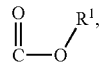

$R^1$ and $R^2$ are each independently chosen from H, and $C_{1-6}$ alkyl, and
$R^5$ is H, $C_1$-$C_6$ alkyl, or $C_1$-$C_3$ alkyl(CO).

In one embodiment of the invention, R4

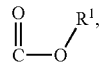

$R^1$ is methyl, and $R^5$ is methyl or hydrogen.

A further embodiment of the invention is the process described above, wherein the 2-fluorolactam of Formula V is prepared with stereoselectivity of at least 90:10 of 2β: 2α. The preferred solvent for this process is methylenechloride, tetrahydrofuran, acetone, N,N-dimethylformamide, N,N-dimethylacetamide, or a mixture of these solvents, such as for example, 6:1 of methelynechloride/acetonitrile. In an embodiment of the claimed process, tetrahydrofuran, acetone, N,N-dimethylformamide, N,N-dimethylacetaride, or 6:1 methelynechloride/acetonitrile is the solvent and 1.1 to 1.5 equivalents of silver (I) fluoride are used. A further embodiment is the process wherein N,N-dimethylformamide is the solvent and 1.1 equivalents of silver (I) fluoride is used. Another embodiment is process described above wherein the process is carried out at room temperature and the 2-fluorlactam is formed with stereoselectivity of at least 94:6 of 2β: 2α.

Alternatively, in another embodiment of the invention preparation of a 2-fluorolactam of Formula V' can be executed as via use of Deoxo-Fluor®,

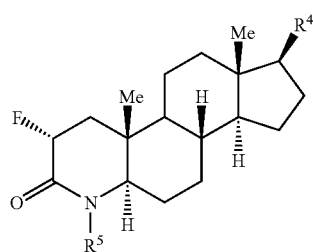

V' which comprises
1) treating a 2-iodolactam of Formula VI with water/DMF followed by NaHCO₃ to form a hydroxyl lactam of Formula XVIII

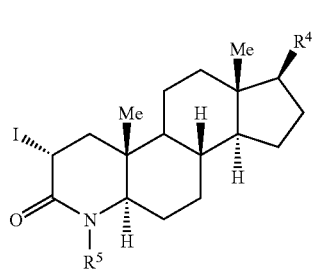

VI wherein R4 is

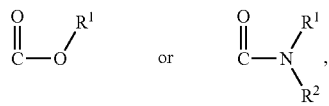

$R^1$ and $R^2$ are each independently chosen from H, and $C_{1-6}$ alkyl,
$R^5$ is H, $C_1$-$C_6$alkyl, or $C_1$-$C_3$alkyl(CO),

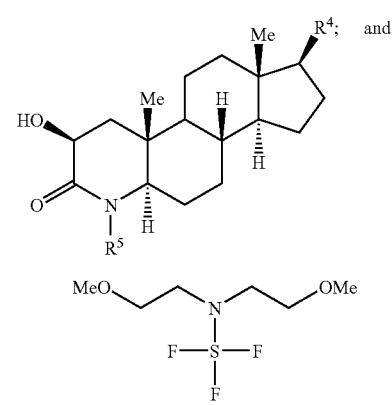

XVIII; and (Z)

2) treating the hydroxyl lactam (XVIII) with a compound of Formula Z, to form a 2-fluoro lactam of Formula V'.
In one variant of this embodiment, R4 is

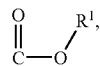

$R^1$ and $R^2$ are each independently chosen from H, and $C_{1-6}$ alkyl, and $R^5$ is H, $C_1$-$C_6$alkyl, or $C_1$-$C_3$alkyl(CO), The invention further encompasses a process for preparing a compound of Formula VII,

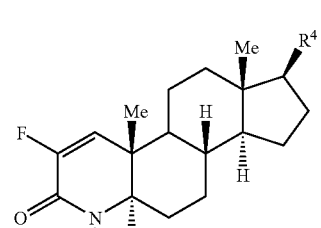

VII

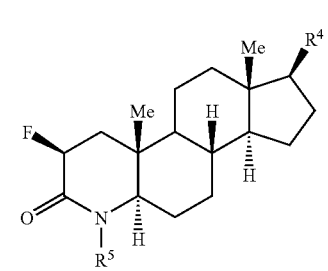

V

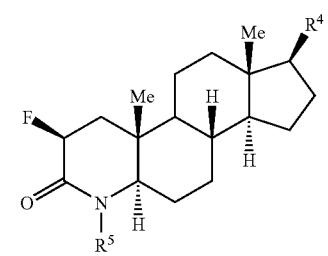

V' which comprises the steps of (1) treating a compound of one of the Formulae V (or V') with lithiumhexamethyldisalizide to afford an enolate; (2) reacting the enolate with methylbenzenesulfinate; and (3) warming to produce the compound of Formula VII, wherein $R^4$ is:

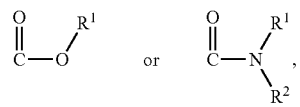

$R^1$ and $R^2$ are each independently chosen from H, and $C_{1-6}$ alkyl, and
$R^5$ is H, $C_1$-$C_6$ alkyl, or $C_1$-$C_3$ alkyl(CO).

Also encompassed by the present invention is a process for preparing an aza-steroid amide of Formula VIII from an aza-steroid acid of Formula IX,

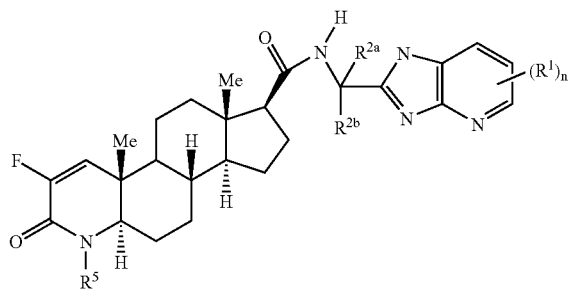

VIII

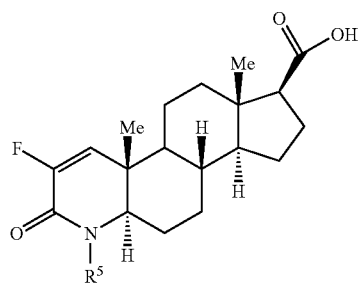

IX which comprises coupling of acid DC with an imidazopyridine methanamine of Formula I,

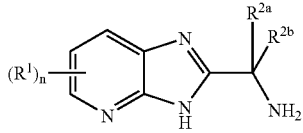

I using 1-(3-dimethylaminopropyl)-3-ethylcarbodiimide hydrochloride or CDI as a coupling agent, wherein n is 0, 1, 2, or 3;
$R^1$ is independently $C_1$-$C_6$ alkyl, halo, $C_1$-$C_3$ perfluoroalkyl, $C_1$-$C_3$ alkyl(CO), or $C_1$-$C_6$ alkyloxy;
$R^{2a}$ and $R^{2b}$ are independently H, $C_1$-$C_6$ alkyl, $C_1$-$C_3$ perfluroalkyl, or halo; and
$R^5$ is H, $C_1$-$C_6$ alkyl, or $C_1$-$C_3$ alkyl(CO).

Yet another embodiment is a process for preparing an aza-steroid amide of Formula X

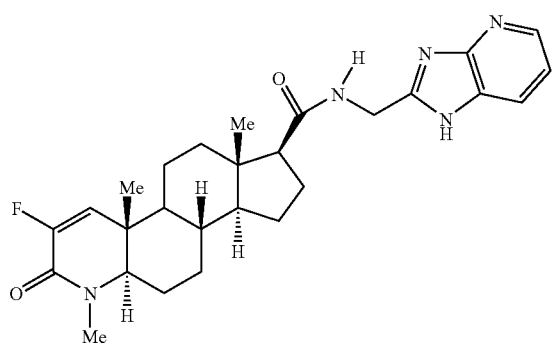

X which comprises:

(1) iodinating compound XI to afford a 2-iodo compound XII;

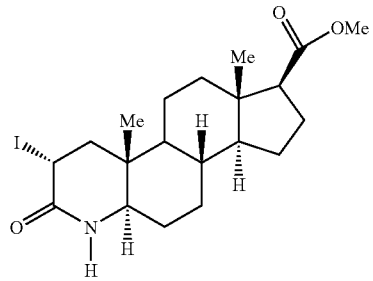

XI

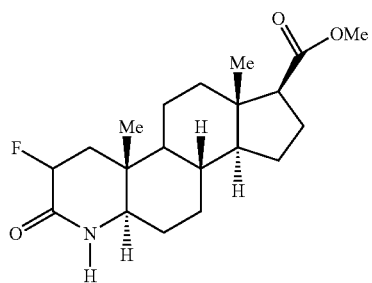

XII (2) displacing the iodine in compound XII with fluorine to afford a 2-fluoro compound XIII;

XIII

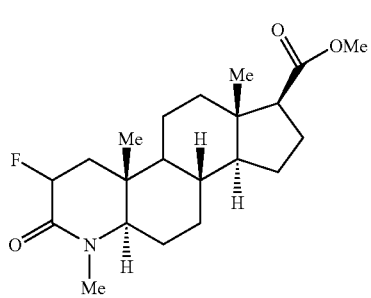

(3) methylating the lactam nitrogen of compound XIII to afford compound XIV;

XIV (4) oxidizing compound XIV to afford compound XV

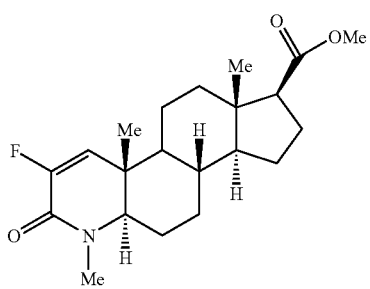

XV (5) hydrolyzing ester XV to afford acid XVI; and

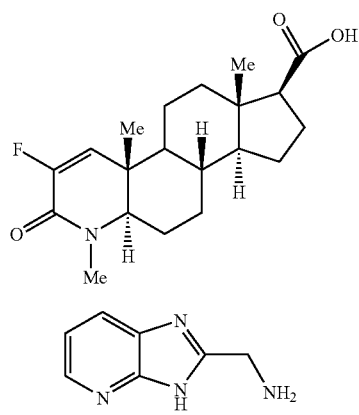

XVI (6) coupling of acid XVI with amine XVII to afford aza-steroid amide

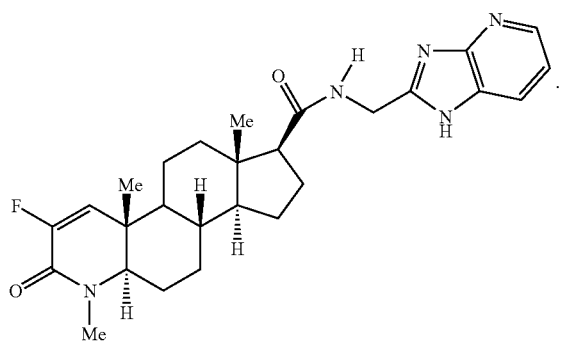

X

The invention further encompasses the process described above, wherein the iodination in (1) comprises the reaction of trimethylsilylchloride and I$_2$; the displacement in (2) comprises the reaction of silver (I) fluoride in dimethylacetamide, dichloromethane, dichloromethane/acetonitrile, or acetonitrile; the methylation of (3) comprises the reaction of t-BuOK and MeI; the oxidation of (4) comprises the reaction of lithiumhexamethyldisilazide and methylbenzenesulfinate; the hydrolysis in (5) comprises the reaction of NaOH or KOH; and the coupling in (6) comprises the reaction of 1-(3-dimethylaminopropyl)-3-ethylcarbodiimide hydrochloride or 1,1'-carbonyldiimidazole.

In a variant of the embodied process described above, the iodination in (1) comprises the reaction of trimethylsilylchloride and I$_2$; the displacement in (2) comprises the heating the iodo compound of (1) with wet DMF (H$_2$O/DMF) followed upon treatment with Deoxo-Fluor® (see formula Z); the methylation of (3) comprises the reaction of t-BuOK and MeI; the oxidation of (4) comprises the reaction of lithiumhexamethyldisilazide and methylbenzenesulfinate; the hydrolysis in (5) comprises the reaction of NaOH or KOH; and the coupling in (6) comprises the reaction of 1-(3-dimethylaminopropyl)-3-ethylcarbodiimide hydrochloride or 1,1'-carbonyldiimidazole.

The chemical structure of Deoxo-Fluor® is

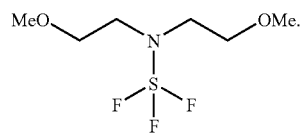

(Z)

The compounds prepared via the present invention may be chiral as a result of asymmetric centers, chiral axes, or chiral planes as described in: E. L. Eliel and S. H. Wilen, *Stereochemistry of Carbon Compounds*, John Wiley & Sons, New York, 1994, pages 1119-1190), and may occur as single optical isomers or as mixtures of any number of the possible optical isomers, including racemates, racemic mixtures, diastereomers, diastereomeric mixtures, enantiomers, and enantiomeric mixtures. In certain instances, the compounds disclosed may exist as tautomers and both tautomeric forms are intended to be encompassed by the scope of the invention, even though only one tautomeric structure is depicted. For example, any claim to compound A below is understood to include tautomeric structure B, and vice versa, as well as mixtures thereof. Here, X represents the remainder of the fluorinated 4-azasteroid derivatives of the present invention.

The term "alkyl" shall mean a straight or branched chain hydrocarbon radical of one to ten carbon atoms, unless the number of carbon atoms is specifically indicated otherwise. Examples of "alkyl" include, but are not limited to, methyl, ethyl, 1-propyl, 2-propyl, n-butyl, sec-butyl, t-butyl, and so on. An alkyl radical with five carbon atoms, for example, would be indicated as "C$_5$-alkyl" and may be straight chained or branched.

The term "alkoxy," as used herein, refers to straight or branched chain alkoxides of the number of carbon atoms specified (e.g., C$_{1-5}$ alkoxy), or any number within this range (i.e., methoxy, ethoxy, etc.).

The term "halogen" and "halo" shall include iodine, bromine, chlorine, and fluorine.

When any variable (e.g., $R^2$, $R^3$, etc.) occurs more than one time in any substituent or in any compound of a specified formula, its definition at each occurrence is independent of its definition at every other occurrence. Also, combinations of substituents and variables are permissible only if such combinations result in stable compounds.

The term "perfluoralkyl" indicates that all the hydrogen atoms in the corresponding alkyl are replaced with fluorine atoms.

The compounds afforded by the instant invention are useful intermediates in the production of androgen receptor modulating compounds or are themselves androgen receptor modulating compounds useful for treating conditions caused by androgen deficiency or which can be ameliorated by androgen replacement, including, but not limited to osteoporosis, osteopenia, glucocorticoid-induced osteoporosis, periodontal disease, bone fracture, bone damage following bone reconstructive surgery, sarcopenia, frailty, aging skin, male hypogonadism, postmenopausal symptoms in women, atherosclerosis, hypercholesterolemia, hyperlipidemia, obesity, aplastic anemia and other hematopoietic disorders, arthritic conditions, such as for example, inflammatory arthritis and joint repair, HIV-wasting, prostate cancer, cancer cachexia, muscular dystrophies, premature ovarian failure, and autoimmune disease, alone or in combination with other active agents. Treatment is effected by administration of the final product obtained from the disclosed processes to a mammal in need of such treatment. In addition, these compounds are useful as ingredients in pharmaceutical compositions alone or in combination with other active agents.

It is generally preferable to administer compounds of the present invention in their enantiomerically pure form. Racemic mixtures can be separated into their individual enantiomers by any of a number of conventional methods. These include chiral chromatography, derivatization with a chiral auxiliary followed by separation by chromatography or crystallization, and fractional crystallization of diastereomeric salts.

The term "pharmaceutically acceptable salts" refers to salts prepared from pharmaceutically acceptable non-toxic bases or acids including inorganic or organic bases and inorganic or organic acids. Salts derived from inorganic bases include aluminum, ammonium, calcium, copper, ferric, ferrous, lithium, magnesium, manganic salts, manganous, potassium, sodium, zinc, and the like. Particularly preferred are the ammonium, calcium, lithium, magnesium, potassium, and sodium salts. Salts derived from pharmaceutically acceptable organic non-toxic bases include salts of primary, secondary, and tertiary amines, substituted amines including naturally occurring substituted amines, cyclic amines, and basic ion exchange resins, such as arginine, betaine, caffeine, choline, N,N'-dibenzylethylenediamine, diethylamine, 2-diethylaminoethanol, 2-dimethylaminoethanol, ethanolamine, ethylenediamine, N-ethyl-morpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, tromethamine, and the like.

When the compound of the present invention is basic, salts may be prepared from pharmaceutically acceptable non-toxic acids, including inorganic and organic acids. Such acids include acetic, benzenesulfonic, benzoic, camphorsulfonic, citric, ethanesulfonic, formic, fumaric, gluconic, glutamic, hydrobromic, hydrochloric, isethionic, lactic, maleic, malic, mandelic, methanesulfonic, malonic, mucic, nitric, pamoic, pantothenic, phosphoric, propionic, succinic, sulfuric, tartaric, p-toluenesulfonic acid, trifluoroacetic acid, and the like. Particularly preferred are citric, fumaric, hydrobromic, hydrochloric, maleic, phosphoric, sulfuric, and tartaric acids.

The following schemes and examples are illustrative of the processes encompassed by the present invention. As will be readily apparent to those in the field, the substituents and substitution patterns on the substrates exemplified herein may be modified without undue experfimentation by the choice of readily available starting materials, reagents, and conventional procedures or variations. As used below and throughout this disclosure, "room temperature" or "RT" indicates that the reaction was performed at ambient temperature without the use of any means for cooling or heating. "Room temperature" is about 25° C.

The illustrative schemes below, therefore, are not limited by the compounds listed or by any particular substituents employed for illustrative purposes. Substituent numbering as shown in the schemes does not necessarily correlate to that used in the claims and often, for clarity, a single substituent is shown attached to the compound in place of multiple substituents which are allowed under the definitions of Formula I defined previously.

The processes of the instant invention are useful in the preparation of imidazopyridyl aza-steroids that are useful as androgen receptor modulators. An especially advantageous preparation of the imidazopyridinylmethanamine sidechains is also disclosed. As illustrated in Scheme A, the imidazopyridine intermediates (A-5) are prepared from an N-protected glycine derivative (A-1), such as N-acylated glycine, which is commercially available, or another suitably protected form of glycine, such as CBZ-glycine, and the appropriate 2,3-diaminopyridine (A-2), which are also readily available, either commercially or synthetically with little effort from those trained in the field. N-acylated glycine is a preferred substrate.

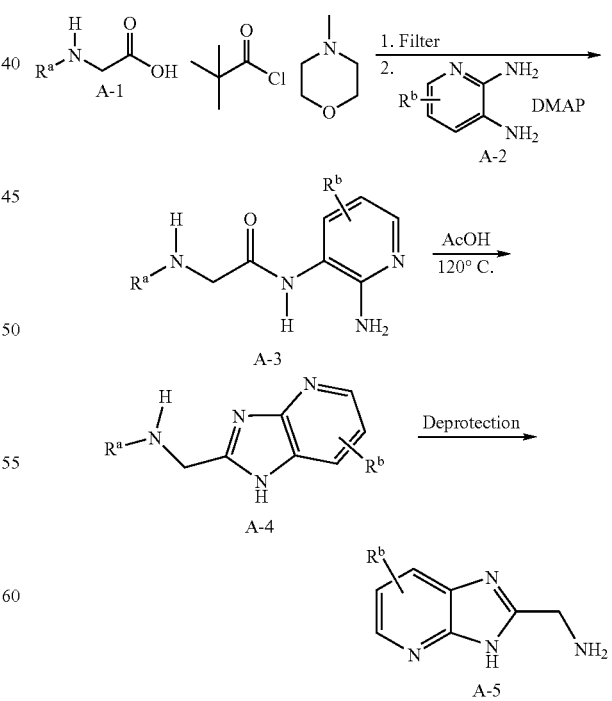

Scheme A

As shown in Scheme A, the N-protected glycine derivative A-1 is coupled with diaminopyridine A-2 to produce A-3. This coupling is accomplished via the use of a carboxy group activating agent, including but not limited to 1,3-dicyclohexylcarbodiimide (DCC) or 1,1'-carbonyldiimidazole (CDI). For example, acid chlorides are especially useful as activating agents in this regard. Reaction of the protected glycine substrate with an acid chloride, such as pivaloyl chloride, produces a mixed anhydride as the reactive intermediate. The use of a base, such as N-methylmorpholine (NMM), in the reaction is useful to absorb any acidic by-product. A beneficial effect of using NMM is that the solid salt by-product of the reaction may be removed by filtration. Subsequent cyclization of A-3 yields the protected imidazopyridine A-4, which can then be deprotected, for example, by addition of an acid in the case of acid labile protecting groups, to afford the desired imidazopyridine A-5. As Scheme A discloses, $R^a$ may be any chemically compatible N-protecting group. Examples of other suitable protecting groups and corresponding deprotection schemes are illustrated in *Protective Groups in Organic Synthesis* by Theodora W. Green (John Wiley & Sons, 1981). Likewise, $R^b$ may be any compatible substituent that would be desirable in the target androgen receptor modulator.

The synthesis of the steroid portion begins with a fluorination reaction, as shown in Scheme B. The starting material for the synthesis of aza-steroid B-4 is aza-steroid B-1, which is readily available from the 2,3-unsaturated analog (*Journal of Medicinal Chemistry* (1986), 29(11), 2298-315)). The fluorination strategy is based on known iodination methodology (King, A. O.; Anderson, K.; Shuman, R. F.; Karady, S.; Abramson, N. L.; Douglas, A. W. *J. Org. Chem.* 1993, 58, 3384-3386.) followed by fluoride displacement of the iodide.

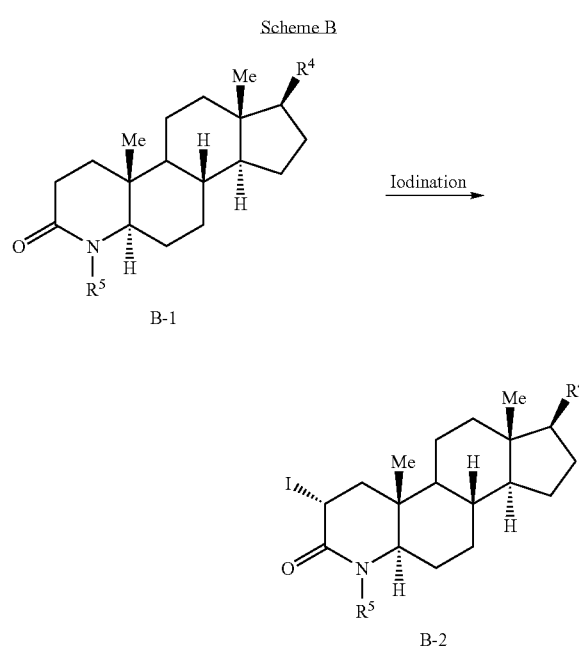

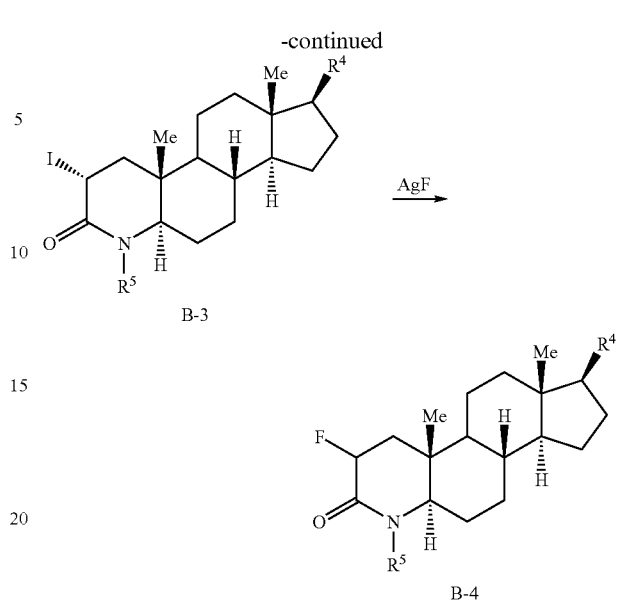

$2a$-iodo lactam B-2 can be obtained as a single stereoisomer. The iodo lactam, B-2, can be converted to the corresponding 2-fluoro lactam by treatment with various sources of fluoride, both organic and inorganic, which include but are not limited to KF, LiF, CsF, $K_2HF$, $BaF_2$, $CaF_2$, $MgF_2$, $NiK_2$, and $Et_3N \cdot 3HF/Et_3N$. These reagents were tested and found to suffer from disadvantages of low conversion and production of undesireable elimination product.

Silver (I) fluoride is known to displace alkyl bromides and iodides to give corresponding fluoro compounds (Pogány, S. A.; Zentner, G. M.; Ringeisen, C. D. Synthesis 1987, 08, 718-719). The literature procedures, however, require 2.5 to 4.5 equiv of silver (I) fluoride. In addition, the reagent's utility with a steroid substrate was unknown. By using 4.5 equiv of AgF in wet acetonitrile at room temperature, the 2-iodo lactam B-2 ($R^5$=H and $R^4$=$CO_2Me$) was completely converted to the corresponding 2-fluoro lactam in an $S_N2$ fashion with high stereoselectivity (2β-fluoro/2α-fluoro=94/6). The amount of AgF required and the reaction rate were very sensitive to the reaction solvent. With the use of dimethylacetamide (DMAC), however, the reaction went to completion within 12 h at room temperature. Surprisingly, only 1.1 equivalents of AgF were necessary. The following summarizes the florination process under varying conditions, using 2-iodo lactam B-2 wherein $R^5$=H and $R^4$=$CO_2Me$:

| Solvent | AgF (equiv) | Reaction Time (h) | % Conversion |
| --- | --- | --- | --- |
| $CH_2Cl_2$ | 2.5 | 7.5 | 100 |
| $CH_2Cl_2$/CAN (6/1) | 1.5 | 48 | 100 |
| THF | 1.5 | 24 | 100 |
| Acetone | 1.5 | 18 | 87 |
| DMF | 1.2 | 12 | 100 |
| DMAc | 1.1 | 12 | 100 |

An alternative synthesis of the steroid portion begins with a fluorination reaction, as shown in Scheme C. The starting material for the synthesis of aza-steroid C-5 is aza-steroid C-1, which is readily available from the 2,3-unsaturated analog (*Journal of Medicinal Chemistry* (1986), 29(11), 2298-315)). The fluorination strategy is based on the iodination methodology followed by fluoride displacement of the iodide. (Lal, G. S.; Pez, G. P.; Pesaresi, R. J.; Prozonic, F. M.; Cheng, H.; *J. Org. Chem.* 1999, 64, 7048-7054.)

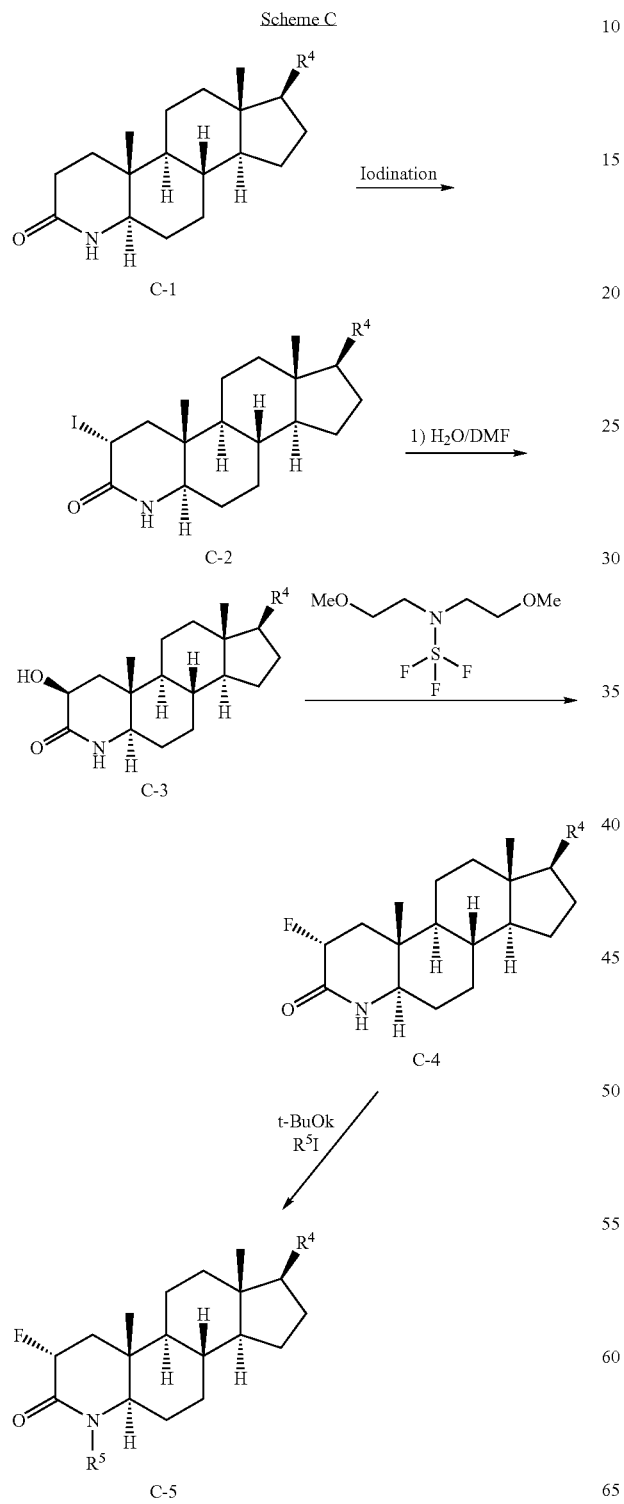

EXAMPLE 1

Preparation of Imidazopyridine Methanamine (1-5)

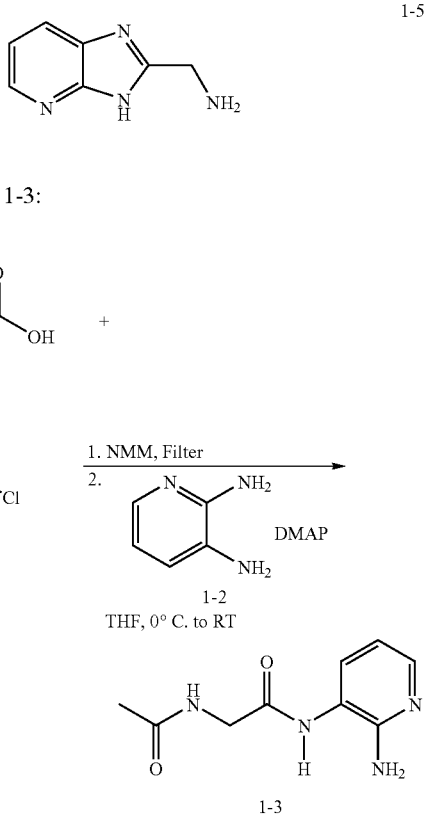

a) Synthesis of 1-3:

300 mL THF were added to a 500 mL three neck flask charged with 48.88 g (0.417 mole) of N-acetyl glycine, 1-1. The resulting slurry was cooled to 0° C. using an ice bath and 50 mL (0.455 mole) of N-methylmorpholine (NMM) were added to the slurry, maintaining the temperature under 5° C. Pivaloyl chloride (50 mL) was then added to the slurry slowly over 30 min, maintaining the temperature under 5° C. The slurry was warmed to 15° C. for 30 minutes, then cooled to 0° C. for 1 h to ensure formation of NMM-HCl salt crystals. The reaction's progress was monitored by checking the supernatant for NMM by GC. The acceptable level of the salt in the supernatant is 15 mg/mL. Upon completion, the slurry was filtered under nitrogen and the solid was washed with THF (90 mL). The yellow filtrate and washes were placed in an addition funnel and used in the next step. Mixed anhydride $^1$H NMR: (400 MHz, DMSO) 8.52 (t), 3.98 (d), 1.87 (s).

To a 1 L three neck flask fitted with a nitrogen inlet, a mechanical stirrer, and a thermocouple was charged 2,3-diaminopyridine 1-2 (30.34 g, 0.278 mole) and DMAP (3.40 g, 0.028 mole). THF (300 mL) was added, followed by NMM (50 mL, 0.455). The yellow mixed anhydride solution obtained above was added dropwise, maintaining the temperature below 25° C. with a water bath. The addition required 45 min. The slurry was filtered after stirring at room temperature for 3 h, washed with THF (75 mL), and dried under nitrogen and vacuum. The product, 1-3, was obtained as a brown powder (51.23 g).

The crude product may be further purified by recrystallization in cases where excess NMM-HCl is present. For example, 19.81 g (83.4 wt %) of crude product was slurried in ethanol (80 mL) and heated to 95° C. Most of the solids dissolved. The solution was allowed to cool while adding MTBE (80 mL) dropwise. The slurry was filtered, washed with MTBE (40 mL), and dried under nitrogen and vacuum. This process yielded 15.97 g of product 1-3 containing 5.2 wt % NMM-HCl salt. 1-3=$^1$H NMR (400 MHz, DMSO): δ=9.15 (s, 1H, NH), 8.19 (t, 1H, NH), 7.78 (d, 1H, pyr), 7.49 (d, 1H, pyr), 6.54 (dd, 1H, pyr), 5.74 (s, 2H, NH2), 3.86 (d, 2H, CH2), 1.88 (s, 3H, CH3)

b) Cyclization of 1-3:

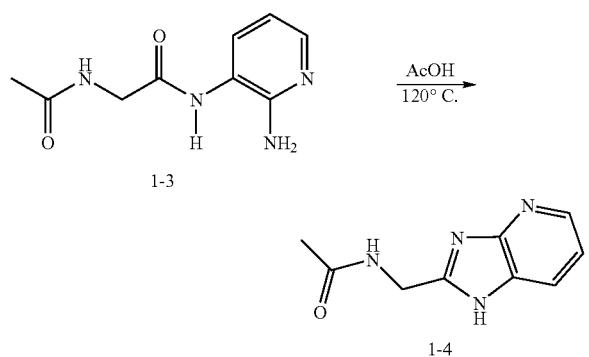

Acetic acid (200 mL) was charged to a 500 mL 3 neck flask fitted with a thermocouple, condenser, and nitrogen line. 46.19 g (0.194 mole) of 1-3 was slowly added to the stirring solvent. The black solution was heated at 120° C. for 10 h. The resulting solution of 1-4 was used directly in the next step. Adding acetic acid to the powder amide resulted in solidification of the powder which must then be broken up manually. Therefore, inverse addition is recommended. HPLC was used used to monitor the reaction until no starting material remained. (Assay yield: 95%).

Typical Retention Times:

Amide: 6.44 min.; Acetyl imidazol: 8.71 min.

c) Deprotection of Acylated Imidazopyridine 1-4

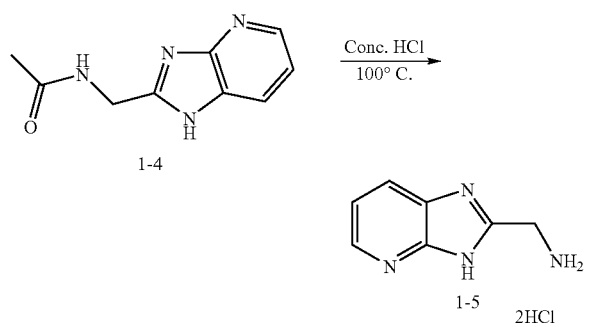

Concentrated HCl was added to the reaction solution from the cyclization reaction above while still at about 120° C. The reaction mixture was then heated heated at 100° C. for 5 h. The reaction was monitored by HPLC. Approximately 2 A% starting material remained at the completion of the reaction which could be driven further by addition HCl. However, the excess water must be removed by distillation after completion of the reaction.

The solution was then distilled to remove 50 mL of solvent and allowed to cool. Drop wise addition of iPAc (200 mL) was commenced while the temperature was still at 100° C. The temperature was then allowed to fall to 8° C. but was maintained at that temperature until the addition of iPAc had been completed. The slurry was allowed to cool slowly and then chilled to 0° C., filtered and washed with iPAc (120 mL). The product 1-5 was obtained as a dark black granular powder (42.87 g).

To remove the color, a carbon treatment was performed. 1.01 g of 1-5 (94.7 wt %, 4.33 mmole) was dissolved in 4:1 methanol/water (10 mL). Darco KB (1.0 g) was added, and the mixture was heated at 50° C. for 1 h. The mixture was then cooled to room temperature, filtered through celite, and washed with methanol (10 mL). The product solution was concentrated, removing 10 mL solvent. THF (20 mL) was added drop wise. The slurry was filtered, washed with THF (2.5 mL), and dried under nitrogen and vacuum. The product was obtained as a light grey powder (830 mg, 87% recovery). 1-5=$^1$H NMR (400 MHz, DMSO): δ=9.09 (bs, 3H, NH), 8.58 (m, 2H, pyr), 7.64 (dd, 1H, pyr), 4.49 (s, 2H, CH2)

EXAMPLE 2

Preparation of Azasteroid 2-7 Utilizing AgF

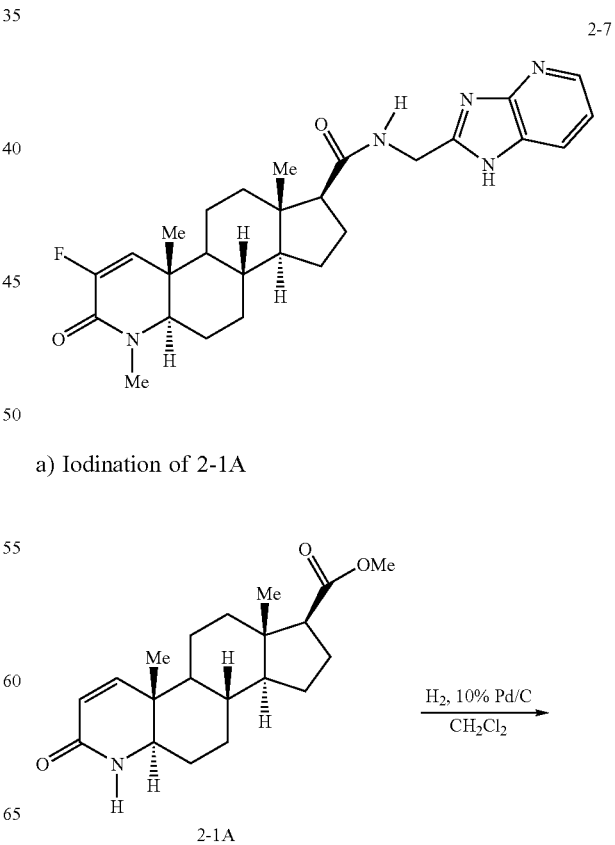

a) Iodination of 2-1A b) Fluorination of 2-2

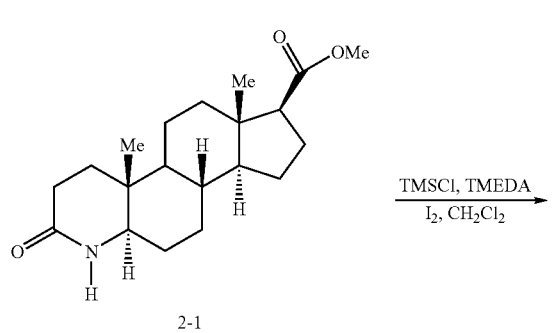

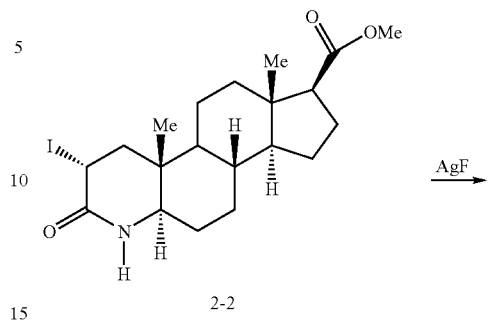

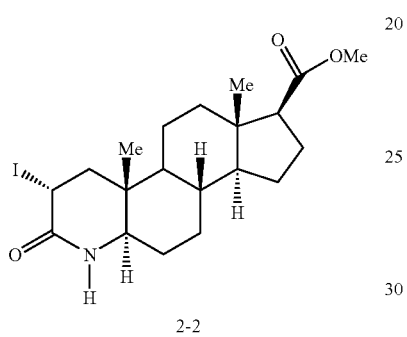

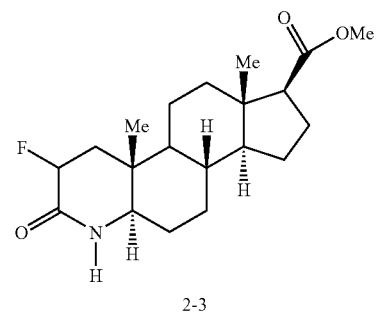

The starting material, lactam 2-1, was prepared by palladium catalyzed hydrogenation of the corresponding unsaturated steroid, 2-1A, according to procedures in the literature. Rasmusson, Gary H.; Reynolds, Glenn F.; Steinberg, Nathan G.; Walton, Edward; Patel, Gool F.; Liang, Tehming; Cascieri, Margaret A.; Cheung, Anne H.; Brooks, Jerry R.; Berman, Charles, *J. Med. Chem.* (1986), 29(11), 2298-315.

To a 3 L flask equipped with nitrogen inlet, mechanical stirrer, and thermocouple was charged 75 g (0.225 mol) of lactam 2-1. 1.12 L dichloromethane were added, followed by 102 mL (0.677 mol) of tetramethylethylenediamine. The solution was cooled to −14° C. using a dry ice/acetone bath. Trimethylsilyl chloride (58 mL, 0.456 mole) was added via an addition funnel over 5 minutes. Iodine (84 g, 0.331 mole) was then added. The dry ice/acetone bath was removed and the reaction mixture was stirred at ambient temperature for 2 h. The reaction was monitored by HPLC until none of the starting lactam could be detected.

The reaction was quenched with 1130 g 10% aq sodium sulfite solution. The mixture was stirred for 20 min. and the two phases were separated. The organic layer was concentrated under vacuum and flushed with acetonitrile (500 mL). The final slurry (<350 mL) was stirred at rt for 30 min. and filtered. The solid was washed with acetonitrile (80 mL) and dried in vacuum oven for about two days to yield 95.2 g (87% yield) of 2-2.

To a 1 L flask equipped with nitrogen inlet, mechanical stirrer, and thermocouple was charged iodo lactam 2-2 (61 g, 0.126 mole). Dichloromethane (500 mL) and acetonitrile (97 mL) were added. To the solution was added silver(I) fluoride (23.7 g, 0.187 mole). The yellow slurry was stirred at ambient temperature until no starting material was detected by HPLC (24-36 h). The slurry was filtered through celite and the celite was washed with dichloromethane (100 mL). The filtrate was assayed by HPLC and concentrated under vacuum to a solid. The solid was dried in a vacuum oven and was used in next step.

N,N-dimethylacetamide (DMAc) may be used as the solvent instead of dichloromethane. To a 50 mL flask equipped with nitrogen inlet, magnetic stir bar, and thermocouple was charged iodo lactam (1.73 g, 95 w %, 3.58 mmole). N,N-Dimethylacetamide (17 mL) was added. To the solution was added silver(I) fluoride (502 mg, 3.95 mmole, 1.1 equiv.). The yellow slurry was stirred at ambient temperature overnight. LC assay indicated complete conversion. The slurry was poured into a flask containing dichloromethane (100 mL) and brine (10%, 30 mL). The mixture was stirred at ambient temperature for 30 min and filtered through celite. The celite was washed with dichloromethane (20 mL). The filtrate was phase-cut and the organic layer was assayed by HPLC. The organic layer was concentrated to an oil. Water (15 mL) was added dropwise. The slurry was stirred at ambient temperature and filtered. 1.25 g of solid was collected (83.5 wt %, 83% β-fluoro lactam and 4.7% α-fluoro lactam).

c) Methylation of 2-3

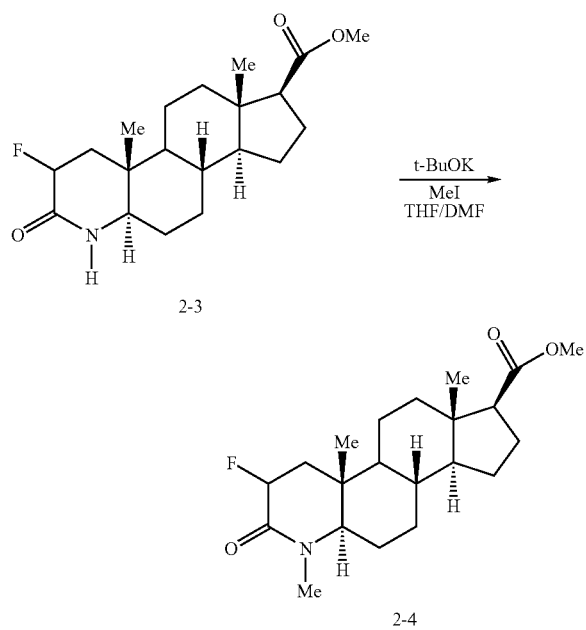

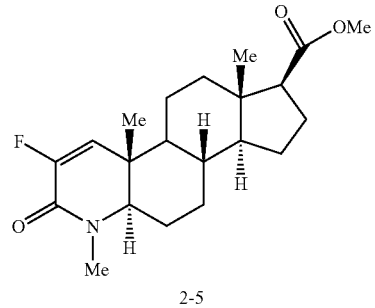

To a 1 L flask equipped with nitrogen inlet, mechanical stirrer, addition funnel, and thermocouple was charged fluoro N—H lactam 2-3 (62.1 g, 0.157 mole), THF (336 mL), and DMF (67 mL). The slurry (Kf=190 ppm) was cooled to −30° C. using dry ice/acetone bath. t-BuOK (1.0 M in THF, 189 mL, 0.189 mole) was added via addition funnel over 15 min and the batch aged at −15° C. for 20 min.

The batch temperature increased to −15° C. at the end of addition. The reaction mixture turned into a clear solution after addition of t-BuOK and aging. Iodomethane (MeI) (13.7 mL, 0.220 mole) was added dropwise. The cooling bath was removed after addition and the batch was stirred at ambient temperature for 1 h. The batch was poured into deionized water (DI water) (370 mL) and the resulting solution was concentrated under vacuum to remove THF. At the end of concentration the batch turned into a slurry. It was diluted with DI water (370 mL) and cooled with ice bath. The slurry was stirred at 5° C. for 30 min. and filtered. The solid was washed with DI water (150 mL) and dried in a vacuum oven at 40° C. for about two days to yields 63.9 g (100% yield) of 2-4, which was used in the next step without further purification.

d) Elimination Reaction

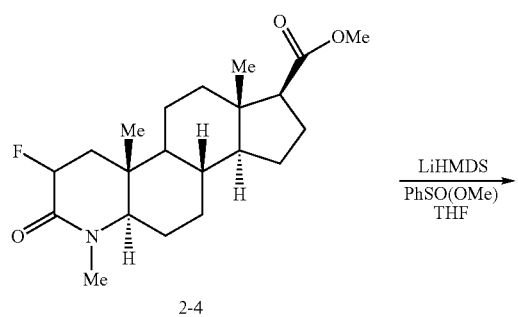

To a 1 L flask equipped with nitrogen inlet, mechanical stirrer, addition funnel, and thermocouple was charged fluoro N-Me lactam 2-4 (36.0 g, 0.0936 mole), THF (360 mL), and methyl benzenesulfinate (15 mL, 0.115 mole). The solution (KF=110 ppm) was cooled to 40° C. using dry ice/acetone bath. The reaction mixture must be appropriately degassed to eliminate exogenous oxygen which can lead to undersirable formation of the 2-keto N-Me lactam. Lithium bis(trimethylsily)amide (LiHMDS) (1.0 M in THF, 120 mL, 0.12 mole) was added via addition funnel over 10 min. The reaction mixture was stirred at −30 −10° C. for 1 h.

The batch temperature increased to −30° C. after addition of LiHMDS. The reaction is usually complete at this point. Otherwise, more reagents (10% additional LiHMDS and methyl benzenesulfinate) can be added to take the reaction to completion.

The batch was warmed to room temperature and quenched with 10% citric acid aqueous solution (270 mL). MTBE (tert-butyl methyl ether) (540 mL) and dichloromethane (540 mL) were added. The mixture was agitated and allowed to settle. The aqueous layer was discarded. The organic layer was heated to reflux for 2 h and then distilled under atmospheric pressure to about half volume.

The batch was concentrated under vacuum. To the residue was added MTBE (100 mL). The slurry was heated to reflux for 30 min. It was cooled slowly to room temperature while heptane (50 mL) was added dropwise via an addition funnel. The slurry was stirred at room temperature for 1 h. More heptane (120 mL) was added dropwise. The slurry was stirred at room temperature for 1 h and filtered. The solid was washed with MTBE/heptane (1:1, 60 mL) and dried under vacuum to afford 30.5 g of product 2-5 as a white solid.

The impurity arising from the 2-keto lactam may be removed by recrystallization. The solid methyl ester (7.8 g) was slurried in 15 mL of isopropyl alcohol (IPA). The slurry was heated to 80° C. Heptane (15 mL) was added. The slurry was stirred at 80° C. for 1 h and cooled to room temperature. Heptane (45 mL) was added dropwise. The slurry was cooled with ice-bath, stirred for 1 h, and filtered to give 7.2 g of purified 2-5 as a solid. (5a,17,)-2-Fluoro-3-oxo-4-methyl-4-azaandrost-1-ene-17-carboxylic acid methyl ester (2-5). $^1$H NMR (400 MHz, CDCl$_3$) δ: 6.17 (d, 1H), 3.68 (s, 3H), 3.44 (dd, 1H), 2.98 (s, 1H), 2.38 (t, 1H), 2.18-2.11 (m, 1H), 2.10-2.06 (m, 1H), 2.04-1.97 (m, 1H), 1.89-1.80 (m, 2H), 1.76-1.55 (m, 4H), 1.45-1.24 (m, 4H), 1.18-1.00 (m, 3H), 0.96 (s, 3H), 0.68 (s, 3H); $^{19}$F NMR (376.5 MHz, CDCl$_3$) δ: -130.3.

e) Hydrolysis of Ester (2-5)

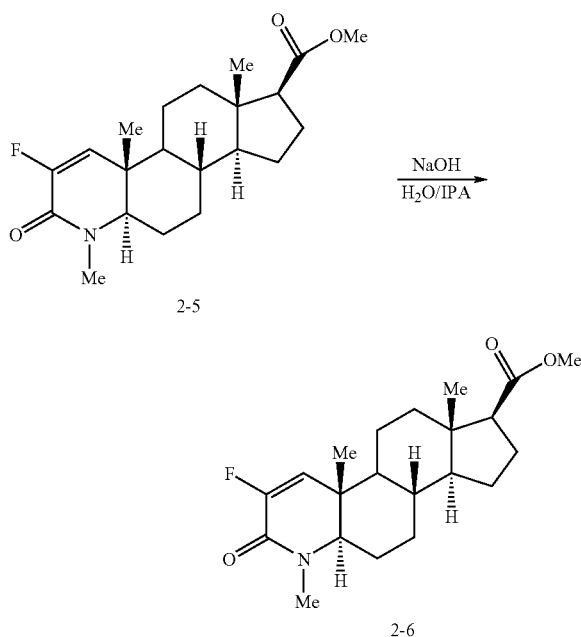

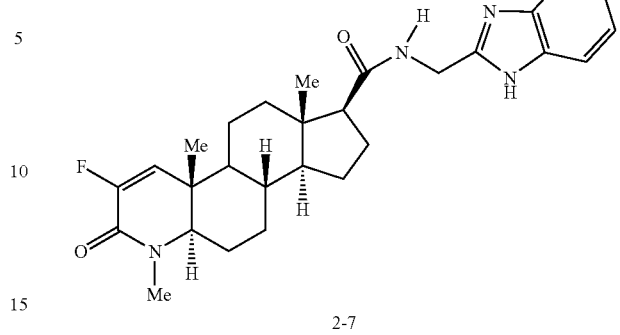

The methyl ester steroid (15.15 g, 95.5 wt %, 0.0417 mole) was charged to a flask with isopropyl alcohol (75 mL). Sodium hydroxide solution was added with stirring. The slurry was refluxed at 80° C. for 3 h and the resulting solution was cooled to room temperature.

The pH of the two phase solution was adjusted to 1 by addition of 1 N HCl (225 mL) dropwise with stirring. The temperature of the mixture was maintained under 25° C. using a water bath. The slurry was filtered and washed with water (40 mL). The product was allowed to dry under nitrogen and vacuum over night to afford 13.79 g of 2-6 in 95% isolated yield. (5α,17β)-2-Fluoro-3-oxo-4-methyl-4-azaandrost-1-ene-17-carboxylic acid (2-6). $^1$H NMR (400 MHz, CDCl$_3$) δ: 6.20 (d, 1H), 3.44 (dd, 1H), 2.99 (s, 1H), 2.43 (t, 1H), 2.16-2.09 (m, 2H), 2.05-1.99 (m, 1H), 1.93-1.82 (m, 2H), 1.78-1.55 (m, 4H), 1.46-1.25 (m, 4H), 1.22-1.05 (m, 4H), 1.00 (s, 3H), 0.72 (s, 3H), $^{19}$F NMR (376.5 MHz, CDCl$_3$) δ: -130.3.

f) Coupling of (1-5) and (2-6)

To a 100 mL flask equipped with nitrogen inlet and magnetic stir bar was charged steroid acid 2-6 (12.1 g, 0.0156 mole). Acetonitrile (60 mL) was added. To the slurry was added 3.8 g (0.0172 mole) of amine 1-5, NMM (6.9 mL, 0.0626 mole), DMAP (0.191 g, 0.0016 mole), and EDC (3.59 g, 0.0187 mole). The slurry was stirred at ambient temperature overnight. The reaction mixture was then poured into water (300 mL). The pH of the mixture was adjusted to 2 with 6 N HCl solution. A clear yellow solution was obtained at this point. The solution was concentrated under vacuum, affording a slurry. The slurry was stirred at room temperature for 1 h and filtered. The solid was washed with water to afford 6.9 g of solid (82.5% yield). The solid was slurried in IPA (10 mL) and acetone (60 mL). The mixture was heated to reflux for 5 h, cooled to room temperature, stirred for 2 h, and filtered. The solid was washed with acetone to yield 5.92 g of 2-7. (2-7, Mass spectrum Measured [M+H]: 480.2763)

Alternatively, CDI can be used as the activating agent for the coupling reaction. The steroid acid 2-6 (500 mg, 1.43 mmole) was slurried in acetonitrile (5 mL). CDI was added at ambient temperature. The reaction mixture was stirred at ambient temperature for 3 h. 1-5 was added (350 mg, 1.58 mmole) followed by N-methylmorpholine (0.35 mL, 3.17 mmole). The slurry was heated to reflux for 3 h, then cooled to ambient temperature and stirred overnight. The reaction mixture was dissolved in MeOH. (28 mL) and assayed 618 mg product (90% yield).

EXAMPLE 3

Preparation of Fluorinated Azasteroid (2-4) Utilizing Deoxo-Fluor®

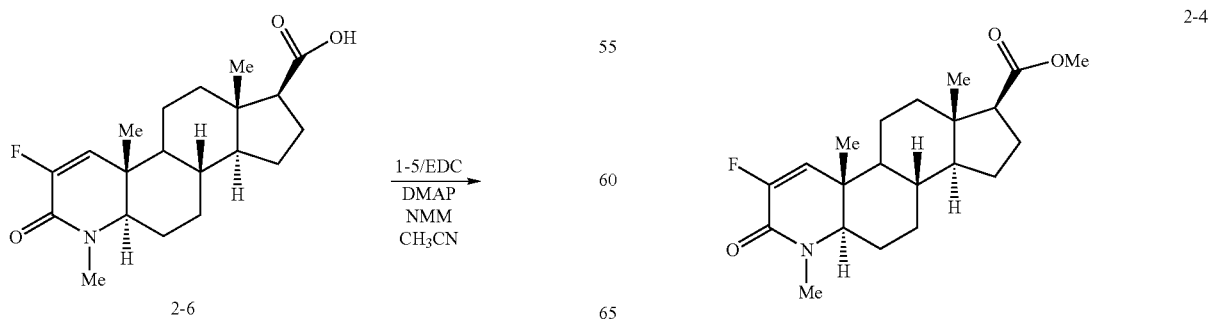

a) Iodination of 2-1A

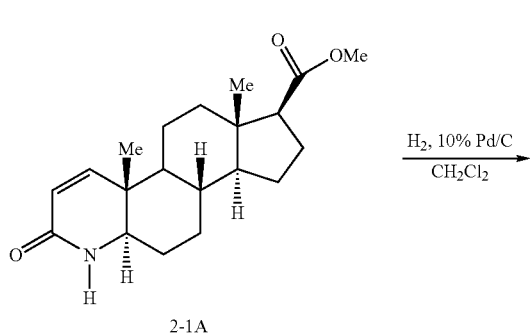

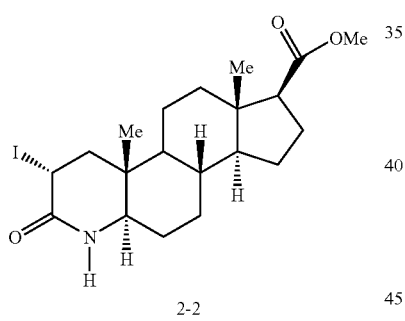

The iodination step is executed in a similar manner to that described in Example 2.

b) Fluorination of 2-2 to form 3-

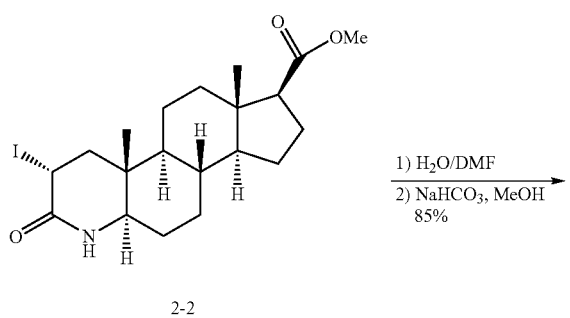

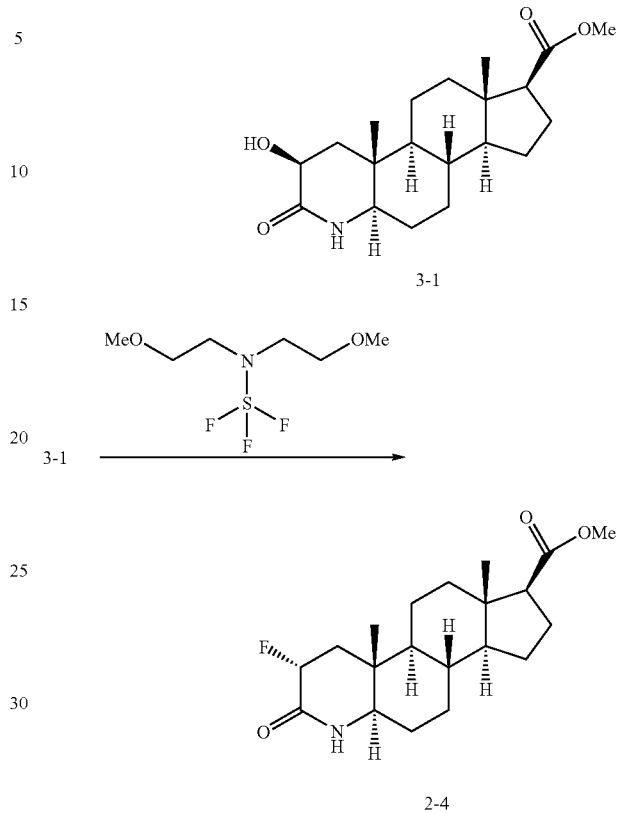

To a 25 mL flask was charged 2-2 (1.45 g, 93 weight %, 2.9 mmole). DMF (15 mL) and water (1.5 mL) was added. The reaction mixture was heated to 110° C. and stirred for 4 h. To the mixture was added saturated $NaHCO_3$ solution (5 mL) and MeOH (8 mL). The reaction mixture was stirred at 60° C. for 3 h, cooled to rt, and poured into water (80 mL). The mixture was concentrated under vacuum to remove MeOH. The slurry was stirred at rt for 30 min. and filtered. The solid (3-1) was washed with water and dried under vacuum to give 860 mg of product as a white solid. mp: 284.7-286.0° C.; $^1$H NMR (400 MHz, $CDCl_3$) δ: 6.47 (br, 1H), 4.17 (dd, 1H, J=4.7, 10.1 Hz), 3.76 (s, 1H), 3.66 (s, 3H), 3.05 (ddd, 1H, J=2.6, 3.8, 12.3 Hz), 2.34 (t, 1H, J=9.3 Hz), 2.18-1.94 (m, 3H), 1.86-1.64 (m, 5H), 1.58-1.20 (m, 6H), 1.11-0.93 (m, 2H), 0.87-0.81 (m, 1H), 0.85 (s, 3H), 0.64 (s, 3H); $^{13}$C NMR (100 MHz, $CDCl_3$) δ: 174.9, 174.3, 65.4, 58.4, 55.3, 55.1, 51.8, 51.3, 44.2, 43.2, 38.1, 37.5, 35.0, 29.6, 26.3, 24.3, 23.5, 21.4, 13.8, 13.5. HR-MS m/z calcd. for $C_{20}H_{32}NO_4$ ($[M+H]^{\oplus}$) 350.2331, found 350.2328.

To a 10 mL flask was charged 3-1 (220 mg, 0.63 mmole), Dichloromethane (2 mL) was added. Deoxo-Fluor® (50 weight % in toluene, 310 mg, 0.70 mmole, 1.1 equiv.) was added. The reaction mixture was stirred at rt for 2 h and quenched with saturated $NaHCO_3$ solution. The mixture was extracted with EtOAc. The organic layer was concentrated under vacuum and the residue was purified by column chromatography on silica gel (20% acetone in $CH_2Cl_2$ as mobile phase) to give 155 mg of product as a white solid (2-4). mp: 269.3-270.1° C.; $^1$H NMR (400 MHz, $CDCl_3$) δ:

7.15 (br, 1H), 4.87 (ddd, 1H, J=7.4, 10.8, 46.8 Hz), 3.64 (s, 3H), 3.17 (dd, 1H, J=3.6, 12.5 Hz), 2.46 (ddd, 1H, J=1.5, 7.5, 12.5 Hz), 2.33 (t, 1H, J=9.4 Hz), 2.15-1.97 (m, 2H), 1.83-1.51 (m, 6H), 1.47-1.20 (m, 5H), 1.15-1.08 (m, 1H), 1.03-0.87 (m, 2H), 0.96 (s, 3H), 0.64 (s, 3H); $^{13}$C NMR (100 MHz, CDCl$_3$) δ: 174.2 168.9, 168.7, 86.7, 84.9, 61.1, 55.1, 55.0, 51.2, 50.9, 44.1, 40.7, 40.5, 38.0, 37.9, 37.9, 34.3, 29.3, 26.3, 24.2. 23.5, 21.0, 13.5, 12.3; $^{19}$F NMR (376.5 MHz, CDCl$_3$) δ: −192.4. HR-MS m/z calcd. for $C_{20}H_{31}NO_4F$ ([M+H]$^{\oplus}$) 352.2288, found 352.2290.

From 2-4, analogous chemistry as outlined in steps d-f of Example 2 is used to synthesize the final azasteroid product, 2-7.

The following assays are used to characterize the activity of tissue selective androgen receptor modulators that may be prepared by the present invention.

In Vitro and In Vivo Assays for Identification of Compounds with SARM Activity

1. Hydroxylapatite-based Radioligand Displacement Assay of Compound Affinity for Endogenously Expressed AR Materials:

Binding Buffer: TEGM (10 mM Tris-HCl, 1 mM EDTA, 10% glycerol, 1 mM beta-mecaptoethanol, 10 mM Sodium Molybdate, pH 7.2)

50% HAP Slurry: Calbiochem Hydroxylapatite, Fast Flow, in 10 mnM Tris, pH 8.0 and 1 mM EDTA.

Wash Buffer: 40 mM Tris, pH7.5, 100 mM KCl, 1 mM EDTA and 1 mM EGTA.

95% EtOH

Methyltrienolone, [17α-methyl-$^3$H], (R1881*); NEN NET590

Methyltrienolone (R1881), NEN NLP005 (dissolve in 95% EtOH)

Dihydrotestosterone (DHT) [1,2,4,5,6,7-$^3$H(N)]NEN NET453

Hydroxylapatite Fast Flow; Calbiochem Cat#391947

Molybdate=Molybdic Acid (Sigma, M1651)

MDA-MB453 cell culture media:
RPMI 1640 (Gibco 11835-055) w/23.8 mM NaHCO$_3$, 2 mM L-glutamine

| In 500 mL of complete media | Final conc. |
| --- | --- |
| 10 mL (1M Hepes) | 20 mM |
| 5 mL (200 mM L-glu) | 4 mM |
| 0.5 mL (10 mg/mL human insulin) in 0.01 N HCl Calbiochem#407694-S) | 10 μg/mL |
| 50 mL FBS (Sigma F2442) | 10% |
| 1 mL (10 mg/mL Gentamicin Gibco#15710-072) | 20 μg/mL |

Cell Passaging:

Cells (Hall R. E., et al., *European Journal of Cancer*, 30A: 484490 (1994)) are rinsed twice in PBS, phenol red-free Trypsin-EDTA is diluted in the same PBS 1:10. The cell layers are rinsed with 1× Trypsin, extra Trypsin is poured out, and the cell layers are incubated at 37° C. for ~2 min. The flask is tapped and checked for signs of cell detachment. Once the cells begin to slide off the flask, the complete media is added to kill the trypsin. The cells are counted at this point, then diluted to the appropriate concentration and split into flasks or dishes for further culturing (Usually 1:3 to 1:6 dilution).

Preparation of MDA-MB453 Cell Lysate

When the MDA cells are 70 to 85% confluent, they are detached as described above, and collected by centrifuging at 1000 g for 10 min at 4° C. The cell pellet is washed twice with TEGM (10 mM Tris-HCl, 1 mM EDTA, 10% glycerol, 1 mM beta-mercaptoethanol, 10 mM Sodium Molybdate, pH 7.2). After the final wash, the cells are resuspended in TEGM at a concentration of $10^7$ cells/mL. The cell suspension is snap frozen in liquid nitrogen or ethanol/dry ice bath and transferred to −80° C. freezer on dry ice. Before setting up the binding assay, the frozen samples are left on ice-water to just thaw (~1 hr). Then the samples are centrifuged at 12,500 g to 20,000 g for 30 min at 4° C. The supernatant is used to set-up assay right away. If using 50 μL of supernatant, the test compound can be prepared in 50 μL of the TEGM buffer.

Procedure for Multiple Compound Screening:

1× TEGM buffer is prepared, and the isotope-containing assay mixture is prepared in the following order: EtOH (2% final concentration in reaction), $^3$H-R1881 or $^3$H-DHT (0.5 nM final Conc. in reaction) and 1× TEGM. [eg. For 100 samples, 200 μL (100×2) of EtOH+4.25 μL of 1:10 $^3$H-R1881 stock+2300 μL (100×23) 1× TEGM]. The compound is serially diluted, e.g., if starting final conc. is 1 μM, and the compound is in 25 μL of solution, for duplicate samples, 75 μL of 4×1 μM solution is made and 3 μL of 100 μM is added to 72 μL of buffer, and 1:5 serial dilution.

25 μL of $^3$H-R1881 trace and 25 μL compound solution are first mixed together, followed by addition of 50 μL receptor solution. The reaction is gently mixed, spun briefly at about 200 rpm and incubated at 4° C. overnight. 100 μL of 50% HAP slurry is prepared and added to the incubated reaction which is then vortexed and incubated on ice for 5 to 10 minutes. The reaction mixture is vortexed twice more to resuspend HAP while incubating reaction. The samples in 96-well format are then washed in wash buffer using The FilterMate™ Universal Harvester plate washer (Packard). The washing process transfers HAP pellet containing ligand-bound expressed receptor to Unifilter-96 GF/B filter plate (Packard). The HAP pellet on the filter plate is incubated with 50 μL of MICROSCINT (Packard) scintillint for 30 minutes before being counted on the TopCount microscintillation counter (Packard). IC$_{50}$s are calculated using R1881 as a reference. Tissue selective androgen receptor modulators of the present invention displayed IC$_{50}$ values of 1 micromolar or less.

2. MMP1 Promoter Suppression, Transient Transfection Assay (TRAMPS).

HepG2 cells are cultured in phenol red free MEM containing 10% charcoal-treated FCS at 37 C with 5% CO$_2$. For transfection, cells are plated at 10,000 cells/well in 96 well white, clear bottom plates. Twenty four hours later, cells are co-transfected with a MMP1 promoter-luciferase reporter construct and a rhesus monkey expression construct (50:1 ratio) using FuGENE6 transfection reagent, following the protocol recommended by manufacturer. The MMP1 promoter-luciferase reporter construct is generated by insertion of a human MMP1 promoter fragment (−179/+63) into pGL2 luciferase reporter construct (Promega) and a rhesus monkey AR expression construct is generated in a CMV- Tag2B expression vector (Stratagene). Cells are further cultured for 24 hours and then treated with test compounds in the presence of 100 nM phorbol-12-myristate-13-acetate (PMA), used to increase the basal activity of MMP1 promoter. The compounds are added at this point, at a range of 1000 nM to 0.03 nM, 10 dilutions, at a concentration on 10×, ¹⁄₁₀th volume (example: 10 microliters of ligand at 10× added to 100 microliters of media already in the well). Cells are further cultured for an additional 48 hours. Cells are then washed twice with PBS and lysed by adding 70 µL of Lysis Buffer (1×, Promega) to the wells. The luciferase activity is measured in a 96-well format using a 1450 Microbeta Jet (Perkin Elmer) luminometer. Activity of test compounds is presented as suppression of luciferase signal from the PMA-stimulated control levels. $EC_{50}$ and Emax values are reported. Tissue selective androgen receptor modulators of the present invention activate repression typically with sub-micromolar $EC_{50}$ values and Emax values greater than about 50%.

REFERENCES a. Newberry E P, Willis D, Latifi T, Boudreaux J M, Towler D A, "Fibroblast growth factor receptor signaling activates the human interstitial collagenase promoter via the bipartite Ets-AP1 element," *Mol. Endocrinol.* 11: 1129-44 (1997).
b. Schneikert J, Peterziel H, Defossez P A, Klocker H, Launoit Y, Cato A C, "Androgen receptor-Ets protein interaction is a novel mechanism for steroid hormone-mediated down-modulation of matrix metalloproteinase expression," *J. Biol. Chem.* 271: 23907-23913 (1996).

3. A Mammalian Two-Hybrid Assay for the Ligand-induced Interaction of N-Terminus and C-Terminus Domains of the Androgen Receptor (Agonist Mode)

This assay assesses the ability of AR agonists to induce the interaction between the N-terminal domain (NTD) and C-terminal domain (CTD) of rhAR that reflects the in vivo virilizing potential mediated by activated androgen receptors. The interaction of NTD and CTD of rhAR is quantified as ligand induced association between a Gal4DBD-rh-ARCTD fusion protein and a VP16-rhARNTD fusion protein as a mammalian two-hybrid assay in CV-1 monkey kidney cells.

The day before transfection, CV-1 cells are trypsinized and counted, and then plated at 20,000 cells/well in 96-well plates or larger plates (scaled up accordingly) in DMEM+ 10% FCS. The next morning, CV-1 cells are cotransfected with pCBB1 (Gal4DBD-rhARLBD fusion construct expressed under the SV40 early promoter), pCBB2 (VP16-rhAR NTD fusion construct expressed under the SV40 early promoter) and pFR (Gal4 responsive luciferase reporter, Promega) using LIPOFECTAMINE PLUS reagent (GIBCO-BRL) following the procedure recommended by the vendor. Briefly, DNA admixture of 0.05 µg pCBB 1, 0.05 µg pCBB2 and 0.1 µg of pFR is mixed in 3.4 µL OPTI-MEM (GIBCO-BRL) mixed with "PLUS Reagent" (1.6 µL, GIBCO-BRL) and incubated at room temperature (RT) for 15 min to form the pre-complexed DNA.

For each well, 0.4 µL LIPOFECTAMINE Reagent (GIBCO-BRL) is diluted into 4.6 µL OPTI-MEM in a second tube and mixed to form the diluted LIPO-FECTAMINE Reagent. The pre-complexed DNA (above) and the diluted LIPOFECTAMINE Reagent (above) are combined, mixed and incubated for 15 min at RT. The medium on the cells is replaced with 40/µL /well OPTI-MEM, and 10 µL DNA-lipid complexes are added to each well. The complexes are mixed into the medium gently and incubated at 37° C. at 5% $CO_2$ for 5 h. Following incubation, 200 µL /well D-MEM and 13% charcoal-stripped FCS are added, followed by incubation at 37° C. at 5% $CO_2$ After 24 hours, the test compounds are added at the desired concentration(s) (1 nM –10 µM). Forty eight hours later, luciferase activity is measured using LUC-Screen system (TROPIX) following the manufacturer's protocol. The assay is conducted directly in the wells by sequential addition of 50 µL each of assay solution 1 followed by assay solution 2. After incubation for 40 minutes at room temperature, luminescence is directly measured with 2-5 second integration.

Activity of test compounds is calculated as the Emax relative to the activity obtained with 3 nM R1881. Typical tissue-selective androgen receptor modulators of the present invention display weak or no agonist activity in this assay with less than 50% agonist activity at 10 micromolar.

REFERENCE

He B, Kemppainen J A, Voegel J J, Gronemeyer H, Wilson E M, "Activation function in the human androgen receptor ligand binding domain mediates inter-domain communication with the NH(2)-terminal domain," *J. Biol. Chem.* 274: 37219-37225 (1999).

4. A Mammalian Two-Hybrid Assay For Inhibition of Interaction between N-Terminus and C-Terminus Domains of Androgen Receptor (Antagonist Mode)

This assay assesses the ability of test compounds to antagonize the stimulatory effects of R1881 on the interaction between NTD and CTD of rhAR in a mammalian two-hybrid assay in CV-1 cells as described above.

Forty eight hours after transfection, CV-1 cells are treated with test compounds, typically at 10 µM, 3.3 µM, 1 µM, 0.33 µM, 100 nM, 33 nM, 10 nM, 3.3 nM and 1 nM final concentrations. After incubation at 37° C. at 5% $CO_2$ for 10-30 minutes, an AR agonist methyltrienolone (R1881) is added to a final concentration of 0.3 nM and incubated at 37° C. Forty-eight hours later, luciferase activity is measured using LUC-Screen system (TROPIX) following the protocol recommended by the manufacturer. The ability of test compounds to antagonize the action of R1881 is calculated as the relative luminescence compared to the value with 0.3 nM R1881 alone.

5. Trans-Activation Modulation of Androgen Receptor (TAMAR)

This assay assesses the ability of test compounds to control transcription from the MMTV-LUC reporter gene in MDA-MB453 cells, a human breast cancer cell line that naturally expresses the human AR. The assay measures induction of a modified MMTV LTR/promoter linked to the LUC reporter gene.

20,000 to 30,000 cells/well are plated in a white, clear-bottom 96-well plate in "Exponential Growth Medium" which consists of phenol red-free RPMI 1640 containing 10% FBS, 4 mM L-glutamine, 20 mM HEPES, 10 ug/mL human insulin, and 20 ug/mL gentamicin. Incubator conditions are 37° C. and 5% $CO_2$. The transfection is done in batch mode. The cells are trypsinized and counted to the right cell number in the proper amount of fresh media, and then gently mixed with the Fugene/DNA cocktail mix and plated onto the 96-well plate. All the wells receive 200 Tl of medium+lipid/DNA complex and are then incubated at 37° C. overnight. The transfection cocktail consists of serum-free Optimem, Fugene6 reagent and DNA. The manufacturer's (Roche Biochemical) protocol for cocktail setup is followed. The lipid (TI) to DNA (Tg) ratio is approximately 3:2 and the incubation time is 20 min at room temperature. Sixteen to 24 hrs after transfection, the cells are treated with test compounds such that the final DMSO (vehicle) concentration is <3%. The cells are exposed to the test compounds for 48 hrs. After 48 hrs, the cells are lysed by a Promega cell culture lysis buffer for 30-60 min and then the luciferase activity in the extracts is assayed in the 96-well format luminometer.

Activity of test compounds is calculated as the $E_{max}$ relative to the activity obtained with 100 nM R1881.

REFERENCES a. R. E. Hall, et al., "MDA-MB453, an androgen-responsive human breast carcinoma cell line with high androgen receptor expression," *Eur. J. Cancer*, 30A: 484490 (1994).

b. R. E. Hall, et al., "Regulation of androgen receptor gene expression by steroids and retinoic acid in human breast-cancer cells," *Int. J. Cancer.*, 52: 778-784 (1992).

6. In Vivo Prostate Assay

Male Sprague-Dawley rats aged 9-10 weeks, the earliest age of sexual maturity, are used in prevention mode. The goal is to measure the degree to which androgen-like compounds delay the rapid deterioration (~–85%) of the ventral prostate gland and seminal vesicles that occurs during a seven day period after removal of the testes (orchiectomy [ORX]).

Rats are orchiectomized (ORX). Each rat is weighed, then anesthetized by isoflurane gas that is maintained to effect. A 1.5 cm anteroposterior incision is made in the scrotum. The right testicle is exteriorized. The spermatic artery and vas deferens are ligated with 4.0 silk 0.5 cm proximal to the testicle. The testicle is freed by one cut of a small surgical scissors distal to the ligation site. The tissue stump is returned to the scrotum. The same is repeated for the left testicle. When both stumps are returned to the scrotum, the scrotum and overlying skin are sutured closed with 4.0 silk. For Sham-ORX, all procedures excepting ligation and scissors cutting are completed. The rats fully recover consciousness and full mobility within 10-15 minutes.

A dose of test compound is administered subcutaneously or orally to the rat immediately after the surgical incision is sutured. Treatment continues for an additional six consecutive days.

Necropsy and Endpoints:

The rat is first weighed, then anesthetized in a $CO_2$ chamber until near death. Approximately 5 ml whole blood is obtained by cardiac puncture. The rat is then examined for certain signs of death and completeness of ORX. Next, the ventral portion of the prostate gland is located and blunt dissected free in a highly stylized fashion. The ventral prostate is blotted dry for 3-5 seconds and then weighed (VPW). Finally, the seminal vesicle is located and dissected free. The ventral seminal vesicle is blotted dry for 3-5 seconds and then weighed (SVWT).

Primary data for this assay are the weights of the ventral prostate and seminal vesicle. Secondary data include serum LH (luteinizing hormone) and FSH (follicle stimulating hormone), and possible serum markers of bone formation and virilization. Data are analyzed by ANOVA plus Fisher PLSD post-hoc test to identify intergroup differences. The extent to which test compounds inhibit ORX-induced loss of VPW and SVWT is assessed.

7. In Vivo Bone Formation Assay:

Female Sprague-Dawley rats aged 7-10 months are used in treatment mode to simulate adult human females. The rats have been ovariectomized (OVX) 75-180 days previously, to cause bone loss and simulate estrogen deficient, osteopenic adult human females. Pre-treatment with a low dose of a powerful anti-resorptive, alendronate (0.0028 mpk SC, 2x/wk) is begun on Day 0. On Day 15, treatment with test compound is started. Test compound treatment occurs on Days 15-31 with necropsy on Day 32. The goal is to measure the extent to which androgen-like compounds increase the amount of bone formation, shown by increased fluorochrome labeling, at the periosteal surface.

In a typical assay, nine groups of seven rats each are studied.

On Days 19 and 29 (fifth and fifteenth days of treatment), a single subcutaneous injection of calcein (8 mg/kg) is given to each rat.

Necropsy and Endpoints:

The rat is first weighed, then anesthetized in a $CO_2$ chamber until near death. Approximately 5 mL whole blood is obtained by cardiac puncture. The rat is then examined for certain signs of death and completeness of OVX. First, the uterus is located, blunt dissected free in a highly stylized fashion, blotted dry for 3-5 seconds and then weighed (UW). The uterus is placed in 10% neutral-buffered formalin. Next, the right leg is disarticulated at the hip. The femur and tibia are separated at the knee, substantially defleshed, and then placed in 70% ethanol.

A 1-cm segment of the central right femur, with the femoral proximal-distal midpoint ats center, is placed in a scintillation vial and dehydrated and defatted in graded alcohols and acetone, then introduced to solutions with increasing concentrations of methyl methacrylate. It is embedded in a mixture of 90% methyl methacrylate :10% dibutyl phthalate, that is allowed to polymerize over a 48-72 hr period. The bottle is cracked and the plastic block is trimmed into a shape that conveniently fits the vice-like specimen holder of a Leica 1600 Saw Microtome, with the long axis of the bone prepared for cross-sectioning. Three cross-sections of 85 μm thickness are prepared and mounted on glass slides. One section from each rat that approximates the midpoint of the bone is selected and blind-coded. The periosteal surface of each section is assessed for total periosteal surface, single fluorochrome label, double fluorochrome label, and interlabel distance.

Primary data for this assay are the percentage of periosteal surface bearing double label and the mineral apposition rate (interlabel distance(μm)/10 d), semi-independent markers of bone formation. Secondary data include uterus weight and histologic features. Tertiary endpoints may include serum markers of bone formation and virilization. Data are analyzed by ANOVA plus Fisher PLSD post-hoc test to identify intergroup differences. The extent to which test compounds increase bone formation endpoint are assessed.

While the foregoing specification teaches the principles of the present invention, with examples provided for the purpose of illustration, it is understood that the practice of the invention encompasses all of the usual variations, adoptions, or modifications, as being within the scope of the following claims and their equivalents.

What is claimed is:

1. A process for preparing an aza-steroid amide of Formula X

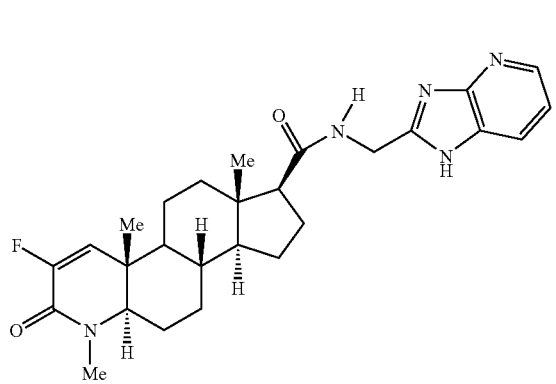

which comprises:
(1) iodinating compound XI to afford a 2-iodo compound XII;

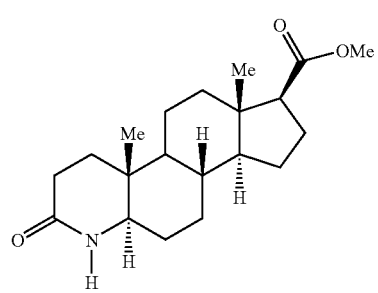

XI (2) displacing the iodine in compound XII with fluorine to afford a 2-fluoro compound XIII;

XII

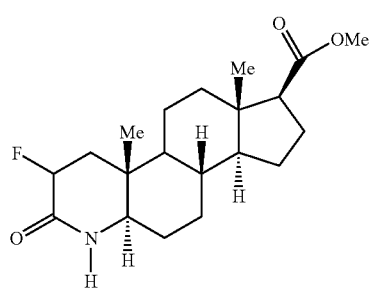

XIII (3) methylating the lactam nitrogen of compound XIII to afford compound XIV;

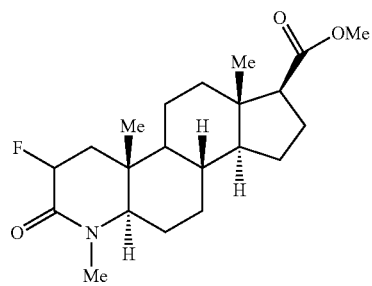

XIV (4) oxidizing compound XIV to afford compound XV;

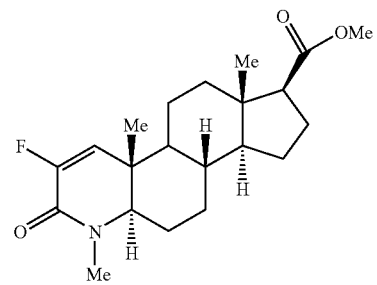

XV (5) hydrolyzing ester XV to afford acid XVI; and

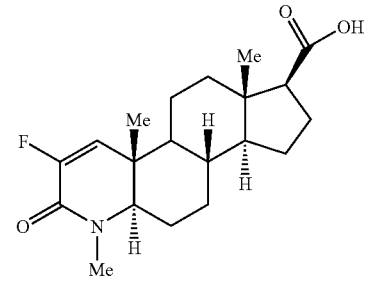

XVI

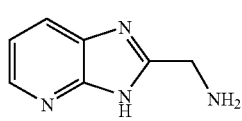

XVII (6) coupling of acid XVI with amine XVII to afford aza-steroid amide X.

2. The process according to claim 1, wherein the iodination in (1) comprises the reaction of trimethylsilyichionde and I₂; the displacement in (2) comprises the reaction of silver (I) fluoride in N,N-dimethylacetamide, dichioromethane, dichioromethane/acetonitrile, or acetonitrile; the methylation of (3) comprises the reaction of t-BuOK and MeI; the oxidation of (4) comprises the reaction of lithiumhexamethyldisilazide and methylbenzenesulfinate; the hydrolysis in (5) comprises the reaction of NaOH or KOH; and the coupling in (6) comprises the reaction of 1-(3-dimethylaminopropyl)-3-ethylcarbodiimide hydrochloride or 1,1'-carbonyldiimazole.

3. The process according to claim 1, wherein the iodination in (1) comprises the reaction of trimethylsilylchloride and $I_2$ to form a 2-iodo lactam product; the displacement in (2) comprises the conversion of the 2-iodo lactam product formed in step (1) by treatment with N,N-dimethyl formamide (DMF) and water, followed by treatment with Deoxo-Fluor®; the methylation of (3) comprises the reaction of t-BuOK and MeI; the oxidation of (4) comprises the reaction of lithiumhexamethyldisilazide and methylbenzenesulfinate; the hydrolysis in (5) comprises the reaction of NaOH or KOH; and the coupling in (6) comprises the reaction of 1-(3-dimethylaminopropyl)-3-ethylcarbodiimide hydrochloride or 1,1'-carbonyldiimidazole.

* * * * *